(12) United States Patent
Kumar et al.

(10) Patent No.: US 9,321,785 B2
(45) Date of Patent: Apr. 26, 2016

(54) METHODS FOR THE TREATMENT OR PROPHYLAXIS OF THROMBOSIS OR EMBOLISM

(71) Applicant: IPCA Laboratories Limited, Mumbai, Maharashtra (IN)

(72) Inventors: Ashok Kumar, Mumbai (IN); Nellithanath Thankachen Byju, Mumbai (IN)

(73) Assignee: IPCA Laboratories Limited, Mumbai (IN)

( * ) Notice: Subject to any disclaimer, the term of this patent is extended or adjusted under 35 U.S.C. 154(b) by 128 days.

(21) Appl. No.: 13/961,514

(22) Filed: Aug. 7, 2013

(65) Prior Publication Data

US 2014/0018331 A1 Jan. 16, 2014

Related U.S. Application Data

(62) Division of application No. 13/219,030, filed on Aug. 26, 2011, now Pat. No. 8,541,422.

(30) Foreign Application Priority Data

Aug. 26, 2010 (IN) .......................... 2388/MUM/2010

(51) Int. Cl.
| | |
|---|---|
| *A61K 31/4365* | (2006.01) |
| *A61K 31/519* | (2006.01) |
| *A61K 31/4709* | (2006.01) |
| *A61K 31/616* | (2006.01) |
| *C07D 495/04* | (2006.01) |
| *A61K 45/06* | (2006.01) |

(52) U.S. Cl.
CPC .......... *C07D 495/04* (2013.01); *A61K 31/4365* (2013.01); *A61K 31/4709* (2013.01); *A61K 31/519* (2013.01); *A61K 31/616* (2013.01); *A61K 45/06* (2013.01)

(58) Field of Classification Search
CPC ........... A61K 2300/00; A61K 31/4709; A61K 31/519; A61K 31/616; A61K 31/4365; A61K 45/06; C07D 495/04
USPC ........................ 514/165, 262.1, 301; 546/114
See application file for complete search history.

(56) References Cited

U.S. PATENT DOCUMENTS

| | | |
|---|---|---|
| 4,740,510 A | 4/1988 | Badorc et al. |
| 5,190,938 A | 3/1993 | Badorc et al. |

FOREIGN PATENT DOCUMENTS

| | | |
|---|---|---|
| CN | 101591344 A1 | 12/2009 |
| CN | 102120744 A | 7/2011 |
| CN | 101885730 A | 11/2011 |
| WO | WO 97/49397 A1 | 12/1997 |
| WO | 2011079407 A1 | 7/2011 |
| WO | 2011095049 A1 | 8/2011 |

OTHER PUBLICATIONS

Anderson, C. D. et al., "Personalized Approaches to Clopidogrel Therapy: Are We There Yet?," American Stroke Association, 2010, vol. 41, No. 12, pp. 2997-3002.
Berger, P. B. et al., "Antiplatelet Therapy: The Role of Platelet Function Testing" at http://www.theHeart.org/documents/sitestructure/en/content/programs/1161429/1161429.html, 2011, pp. 1-15.
Brandt, J. T. et al., "A Comparison of Prasugrel and Clopidogrel Loading Doses on Platelet Function: Magnitude of Platelet Inhibition is Related to Active Metabolite Formation," American Heart Journal, 2007, vol. 153, No. 1, pp. 66e9-66e16.
Chad, D. et al., "A New Era for Antiplatelet Therapy in Patients with Acute Coronary Syndrome," The American Journal of the Medical Sciences, 201, vol. 340, No. 5, pp. 407-411.
Farid, N. A. et al., "Metabolism and Disposition of the Thienopyridine Antiplatelet Drugs Ticlopidine, Clopidogrel, and Prasugrel in Humans," The Journal of Clinical Pharmacology, 2010, vol. 50, No. 2, pp. 126-142.
Giusti, B. et al., "Response to Antiplatelet Treatment: From Genes to Outcome," The Lancet, 2010, vol. 376, No. 9749, pp. 1278-1281.
Hagihara, K. et al., "A Possible Mechanism for the Differences in Efficiency and Variability of Active Metabolite Formation from Thienopyridine Antiplatelet Agents, Prasugrel and Clopidogrel," Drug Metabolism and Disposition, vol. 37, No. 11, pp. 2145-2152.
Von Beckerath, N. et al., "Absorption, Metabolization, and Antiplatelet Effects of 300-, 600-, and 900-mg Loading Doses of Clopidogrel: Results of the ISAR-CHOICE (Intracoronary Stenting and Antithrombotic Regimen: Choose Between 3 High Oral Doses for Immediate Clopidogrel Effect) Trial," Circulations, 2005, vol. 112, No. 19, pp. 2946-2950.
Ingelman-Sunberg, M. et al., "Genetic Polymorphism and Toxicology—with Emphasis on Cytochrome P450," Toxicological Sciences, 2010, pp. 1-30.
Mannheimer, B. et al., "Drug-Drug Interactions that Reduce the Formation of Pharmacologically Active Metabolites: A Poorly Understood Problem in Clinical Practice," Journal of Internal Medicine, 2010, vol. 268, No. 6, pp. 540-548.
Mega, J. L. et al., "Reduced-Function CYP2C19 Genotype and Risk of Adverse Clinical Outcomes Among Patients Treated with Clopidogrel Predominantly for PCI: A Meta-Analysis," Journal of the American Medical Association, 2010, vol. 304, No. 16, pp. 1821-1830.
Nguyen, T. A. et al., "Resistance to Clopidogrel: A Review of the Evidence," Journal of the American College of Cardiology, 2005, vol. 45, No. 8, pp. 1157-1164.

(Continued)

*Primary Examiner* — Savitha Rao
(74) *Attorney, Agent, or Firm* — Baker & Hostetler, LLP

(57) ABSTRACT

The present invention relates to a method of ameliorating the drawbacks of anti-platelet drug named clopidogrel. The method of the present invention comprises administration of an (S)oxo-clopidogrel or its derivative of the Formula IIA in its free or pharmaceutically acceptable salt form for alleviating the symptoms of thrombosis or embolism by inhibiting blood platelet aggregation. Compositions for use in such methods are also provided.

11 Claims, No Drawings

(56) References Cited

OTHER PUBLICATIONS

Periello, J. M. et al., "Structure and Stereochemistry of the Active Metabolite of Clopidogrel," The American Society for Pharmacology and Experimental Therapeutics, 2002, vol. 30, No. 11, pp. 1288-1295.

Plavix Label, Aug. 2010.

Savi, P. et al., "Identification and Biological Activity of the Active Metabolite of Clopidogrel," Thromb Haemost, 2000, vol. 84, pp. 891-896.

Achar, S. et al., "Pharmacokinetics Drug Metabolism, and Safety of Prasugrel and Clopidogrel," Postgraduate Medicine, 2011, vol. 123, No. 1, pp. 73-79.

Angiolillo, D. J. et al., "High Clopidogrel Loading Dose during Coronary Stenting: Effects on Drug Response and Interindividual Variability," European Heart Journal, 2004, vol. 25, pp. 1903-1910.

Bouman, H. J. et al., "Paraoxonase-1 is a Major Determinant of Clopidogrel Efficacy," Nature Medicine, 2011, vol. 17, No. 1, pp. 110-116.

Cadroy, Y. et al., "Early Potent Antithrombotic Effect With Combined Aspirin and a Loading Dose of Clopidogrel on Experimental Arterial Thrombogenesis in Humans," American Heart Association, Circulation, 2000, vol. 101, pp. 2823-2828.

Caplain, H. D. et al., "Pharmacokinetics of Clipidogrel," Seminars in Thrombosis and Hemostasis, 1999, vol. 25, Suppl. 2, Georg Thieme Verlag Stuttgart, NY (publisher), pp. 25-28.

Cattaneo, M., "Fast, potent, and reliable inhibition of platelet aggregation," European Heart Journal Supplements, 2009, vol. 11, Supplement G, pp. G9-G13.

Conrado, D. J. et al., "Role of drug absorption in the pharmacokinetics of therapeutic interventions for stroke," Annals of the New York Academy of Sciences, 2010, vol. 1207, pp. 134-142.

Curzen, N. et al., "Monitoring the effectiveness of antiplatelet therapy: opportunities and limitations," an accepted article for British Journal of Clinical Pharmacology, 2011, pp. 1-39.

Damani, S. B. et al., "The Case for Routine Genotyping in Dual-Antiplatelet Therapy," Journal of the American College of Cardiology, 2010, vol. 56, No. 2, pp. 109-111.

DiGirolamo, G. et al., "Beyond Efficacy: Pharmacokinetic Differences Between Clopidogrel, Prasugrel and Ticagrelor," Expert Opinion on Pharmacotherapy, 2011, pp. 1-11.

Disney, B. R. et al., "Review Article: Proton Pump Inhibitors with Clopidogrel—Evidence for and Against a Clinically-Important Interaction," Alimentary Pharmacology & Therapeutics, 2011, vol. 33, No. 7, pp. 758-767.

Fleisher, D. et al., "Drug, Meal and Formulation Interactions Influencing Drug Absorption After Oral Administration: Clinical Implications," Clinical Pharmacokinetics, 1999, vol. 36, No. 3, pp. 233-254.

Furuta, T., "Risk and Benefit of Proton Pump Inhibitor for Patients Undergoing Anti-Platelet Therapy Including Clopidogrel," Internal Medicine, 2009, vol. 48, pp. 1847-1848.

Gurbel, P. A. et al., "Clopidogrel Loading with Eptifibatide to Arrest the Reactivity of Platelets: Results of the Clopidogrel Loading with Eptifatide to Arrest the Reactivity of Platelets (Clear Platelets) Study," American Heart Association, Circulation, 2005, vol. 111, pp. 1153-1159.

Gurbel, P. A. et al., "Randomized Double-Blind Assessment of the Onset and Offset of the Antiplatelet effects of Ticagrelor Versus Clopidogrel in Patients with Stable Coronary Artery Disease: The Onset/Offset Study," Circulation Journal of the American Heart Association, 2009, vol. 120, pp. 2577-2585, downloaded on Mar. 7, 2011 from http://circ.ahajournals.org.

Hagihara, K. et al., "Comparison of Human Cytochrome P450 Inhibition by the Thienopyridines Prasugrel, Clopidogrel, and Ticlopidine," Drug Metabolite Pharmacokinetics, 2008, vol. 23, No. 6, pp. 412-420.

Hagihara, K. et al., "Comparison of Formation of Thiolactones and Active Metabolites of Prasugrel and Clopidogrel in Rats and Dongs," Xenobiotica, 2009, vol. 39, No. 3, pp. 218-226.

Herbert, J. M. et al., "Clopidogrel, A Novel Antiplatelet and Antithrombotic Agent," Cardiovascular Drug Reviews, 1993, vol. 11, No. 2, pp. 180-198.

Holmes, D. R. et al., "ACCF/AHA Clopidogrel Clinical Alert: Approaches to the FDA "Boxed Warning": A Report of the American College of Cardiology Foundation Task Force on Clinical Expert Consensus Documents and the American Heart Association," Circulation Journal of the American Heart Association, 2010, vol. 122, pp. 537-557.

Husted, S. et al., "Pharmacodynamics, pharmacokinetics, and safety of the oral reversible P2Y12 antagonist AZD6140 with aspirin in patients with atherosclerosis: a double-blind comparison to clopidogrel with aspirin," European Heart Journal, 2006, vol. 27, pp. 1038-1047.

Kim, S. D. et al., "Bioequivalence and Tolerability of Two Clopidogrel Salt Preparations, Besylate and Bisulfate: A Randomized, Open-Label, Crossover Study in Healthy Korean Male Subjects," Clinical Therapeutics, 2009, vol. 31, No. 4, pp. 793-803.

Lins, R. et al., "Pharmacokinetic Profile of 14C-Labeled Clopidogrel," Seminars in Thrombosis and Hemostasis, 1999, vol. 25, Suppl. 2, pp. 29-33.

Makkar, R. R. et al., "Effects of clopidogrel, aspirin and combined therapy in a porcine ex vivo model of high-shear induced sten thrombosis," European Heart Journal, 1999, vol. 19, pp. 1538-1546.

Mohammad, R. A. et al., "Antiplatelet Therapy After Placement of a Drug-Eluting Stent: A Review of Efficacy and Safety Studies," Clinical Therapeutics, 2010, vol. 32, No. 14, pp. 2265-2281.

Nishiya, Y. et al., "Mechanism-Baed Inhibition of Human Cytochrome P450 2B6 by Ticlopidine, Clopidogrel, and the Thiolactone Metabolite of Prasugrel," Drug Metabolism and Disposition, 2009, vol. 37, No. 3, pp. 589-593.

Nishiya, Y. et al., "Comparison of mechanism-based inhibition of human cytochrome P450 2C19 by ticlopidine, clopidogrel, and prasugrel," Xenoblotica, 2009, vol. 39, No. 11, pp. 836-843.

Sada, S. et al., "The prophylactic use of a proton pump inhibitor (PPI) in patients treated with clopidogrel and aspirin for an acute coronary syndrome or placement of a coronary stent reduces the rate of upper gastrointestinal bleeding iwth no apparent increase in cardiovascular events," Internal and Emergency Medicine, Mar. 3, 2011, two pages.

Savi, P. et al., "The Antiaggregating Activity of Clopidogrel is due to a Metabolic Activation by the Hepatic Cytochrome P450-1A," Thrombosis and Haemostasis, 1994, vol. 72, No. 2, pp. 313-317.

Sciascio, G. D. et al., "Effectiveness of In-Laboratory High-Dose Clopidogrel Loading Versus Routine Pre-Load in Patients Undergoing Percutaneous Coronary Intervention," Journal of the American College of Cardiology, 2010, vol. 56, No. 7, pp. 550-557.

Takahashi, S. et al., "Different Inhibitory Effects in Rat and Human Carboxylesterases," Drug Metabolism and Desposition, 2009, vol. 37, pp. 956-961.

Yan, B. P. et al., "Variability in Response to Clopidogrel: How Important are Pharmacogenetics and Drug Interactions?," British Journal of Clinical Pharmacology, 2011, pp. 1-43.

Zairis, M. N. et al., "The impact of treatment with omeprazole on the effectiveness of clopidogrel drug therapy during the first year after successful coronary stenting," Can. J. Cardio., 2010, vol. 26, No. 2, pp. e54-e57.

Terpening, C., "Clopidogrel: A Pharmacogenomic Perspective on its Use in Coronary Artery Disease," Clinical Medicine Insights: Cardiology, 2010, vol. 4, pp. 117-128 available at http://www.la-press.com.

O'Donoghue, M. et al., "Clopidogrel Response Variability and Future Therapies: Clopidogrel Does One Size Fit All?," Circulation, 2006, vol. 114, pp. e600-e606.

Kuliczkowski, W. et al., "Interindividual variability in the response to oral antiplatelet drugs: a position paper of the Working Group on antiplatelet drugs resistance appointed by the Section of Cardiovascular Interventions of the Polish Cardiac Society, endorsed by the Working Group on Thrombosis of the European Society of Cardiology," European Heart Journal, 2009, vol. 30, pp. 426-435.

Angiolillo, D. J. et al., "Variability in Individual Responsiveness to Clopidogrel," Journal of the American College of Cardiology, 2007, vol. 49, No. 14, pp. 1505-1516, downloaded at http://content.onlinejacc.org. on Jan. 7, 2013.

(56) References Cited

OTHER PUBLICATIONS

Willett, K. C. et al., "Thienopyridines in Acute Coronary Syndrome," Annals of Pharmacotherapy, 2011, pp. 207-217.

Scott, S. A. et al., "Identification of CYP2C19*4B: pharmacogenetic implications for drug metabolism including clopidogrel responsiveness," The Pharmacogenomics Journal, 2011, pp. 1-9.

Shand, J. A. et al., "Ticagrelor: from concept to clinical evaluation," Biomarks Med., 2011, vol. 5, No. 1, pp. 53-62.

Sharma, R. K. et al., "Aspirin and clopidogrel hyporesponsiveness and nonresponsiveness in patients with coronary artery stenting," Vascular Health and Risk Management, 2009, vol. 5, pp. 965-972.

Storey, R. F. et al., "Incidence of Dyspnea and Assessment of Cardiac and Pulmonary Function in Patients with Stable Coronary Artery Disease Receiving Ticagrelor, Clopidogrel, or Placebo in the Onset/Offset Study," Journal of the American College of Cardiology, 2010, vol. 56, No. 3, pp. 185-193.

Suh, J.-W. et al., "Increased risk of atherothrombotic events associated with cytochrome P450 3A5 polymorphism in patients taking clopidogrel," CMAJ, 2006, vol. 174, No. 12, pp. 1715-1722.

Taubert, D. et al., "Pharmacokinetics of clopidogrel after administration of a high loading dose," Thrombosis and Haemostasis, 2004, vol. 92, No. 2, pp. 311-316.

Topol, E. J. et al., "Catapulting clopidogrel pharmacogenomics forward," Nature Medicine, 2011, vol. 17, No. 1, pp. 40-41.

Wallentin, L. et al., "Ticagrelor versus Clopidogrel in Patients with Acute Coronary Syndromes," The New England Journal of Medicine, 2009, vol. 361, No. 11, pp. 1045-1057.

White, H. D., "Oral antiplatelet therapy for atherothrombotic disease: Current evidence and new directions," American Heart Journal, 2011, vol. 161, No. 3, pp. 450-461.

Zafar, M. U. et al., "Crushed Clopidogrel Administered via Nasogastric Tube Has Faster and Greater Absorption than Oral Whole Tablets," Journal of Interventional Cardiology, vol. 22, No. 4, pp. 385-389.

"Declaration — B.d.R.203(b)"; United States Patent and Trademark Office, PTAB, Interference No. 106,029; dated Jun. 2, 2015; 29 pages.

"Sun Exhibit 1025"; United States Patent and Trademark Office, PTAB, Interference No. 106,029; dated Oct. 15, 2015; 19 pages.

"Sun Substantive Motion 2"; United States Patent and Trademark Office, PTAB, Interference No. 106,029; dated Oct. 15, 2015; 31 pages.

METHODS FOR THE TREATMENT OR PROPHYLAXIS OF THROMBOSIS OR EMBOLISM

CROSS-REFERENCE TO RELATED APPLICATIONS

This application is a divisional of U.S. patent application Ser. No. 13/219,030, filed Aug. 26, 2011, which issued as U.S. Pat. No. 8,541,422 on Sep. 24, 2013, which application claims the priority of Indian Patent Application No. 2388/MUM/2010, filed Aug. 26, 2010, which is incorporated herein by reference.

FIELD OF INVENTION

The present invention relates to treatment or prophylaxis of thrombosis or embolism. The present invention ameliorates the drawbacks of antiplatelet drugs, such as clopidogrel, by using an (S)-oxo-clopidogrel or its derivative, in its free or pharmaceutically acceptable salt form for alleviating the symptoms of thrombosis and/or embolism by inhibiting blood platelet aggregation.

BACKGROUND OF THE INVENTION

Conditions resulting from thrombotic or thromboembolic events are the leading causes of illness and death in adults in western civilization. Intravascular thrombosis and embolism are common clinical manifestations of many diseases. Unregulated activation of the hemostatic system has the potential to cause thrombosis and embolism, which can reduce blood flow to critical organs like the brain and myocardium. Certain patient groups have been identified that are particularly prone to thrombosis and embolism. These include patients (1) immobilized after surgery, (2) with chronic congestive heart failure, (3) with atherosclerotic vascular disease, (4) with malignancy, or (5) who are pregnant. The majority of "thrombosis prone" individuals have no identifiable hemostatic disorder, although there are certain groups of individuals having inherited or acquired "hypercoaguable" or "prethrombotic" conditions predisposing them to recurrent thrombosis (Harrison's Principles of Internal Medicine, 12th ed. McGraw Hill).

Effective primary hemostasis requires three critical events: platelet adhesion, granule release, and platelet aggregation. Within a few seconds of injury, platelets adhere to collagen fibrils in vascular subendothelium. This interaction is facilitated by von Willebrands factor, an adhesive glycoprotein which allows platelets to remain attached to the vessel wall despite the high shear forces generated within the vascular lumen. Von Willebrand's factor accomplishes this task by forming a link between platelet receptor sites and subendothelial collagen fibrils.

As the primary hemostatic plug is being formed, plasma coagulation proteins are activated to initiate secondary hemostasis. There is little difference between hemostatic plugs, which are a physiological response to injury, and pathologic thrombi. Thrombosis is often described as coagulation which has occurred in the wrong place or at the wrong time. Hemostatic plugs or thrombi that form in veins where blood flow is slow are richly endowed with fibrin and trapped red blood cells and contain relatively few platelets. These thrombi often form in leg veins and can break off and embolize to the pulmonary circulation. Conversely, clots that form in arteries under conditions of high flow are predominantly composed of platelets and have little fibrin. These arterial thrombi may readily dislodge from the arterial wall and embolize to distant sites to cause temporary or permanent ischemia. This is particularly common in the cerebral and retinal circulation and may lead to transient neurologic dysfunction (transient ischemic attacks) including temporary monocular blindness (amaurosis fugax) or strokes. In addition, there is increasing evidence that most myocardial infarctions are due to thrombi which form within atherosclerotic coronary arteries. (The preceding discussion is taken primarily from Harrison's Principles of Internal Medicine, 12th ed., McGraw Hill.)

Extracellular nucleotides and their receptors of platelets are important components of the cardiovascular system and are involved in functions like platelet activation and the control of vascular tone. Adenosine diphosphate (ADP) and Adenosine Triphosphate (ATP), are playing crucial roles in the physiological process of haemostasis and in the development and extension of arterial thrombosis (2). By itself ADP is a weak agonist of platelet aggregation inducing only reversible responses as compared to strong agonists such as thrombin or collagen. However, due to its presence in large amounts in the platelet dense granules and its release upon activation at sites of vascular injury, ADP is an important so-called secondary agonist which amplifies most of the platelet responses and contributes to the stabilization of the thrombus. The receptors for extracellular nucleotides belong to the P2 family which consists of two classes of membrane receptors: P2X ligand-gated cation channels (P2 X 1-7) and Glycoprotein-coupled P2Y receptors (P2Y1, 2, 4, 6, 11, 12, 13, 14). Each of these receptors has a specific function during platelet activation and aggregation, which naturally has implications for their involvement in thrombosis.

Since ADP and ATP play a crucial role in platelet activation, their receptors are potential targets for antithrombotic drugs. The ATP-gated cation channel P2X1 and the two G protein-coupled ADP receptors, P2Y1 and P2Y12, selectively contribute to platelet aggregation and formation of a thrombus. Owing to its central role in the growth and stabilization of a thrombus, the P2Y12 receptor is an established target of antithrombotic drugs mainly the thienopyridine class of compounds like ticlopidine, clopidogrel, prasugrel etc. . . .

The mainstay of antiplatelet therapy for patients with acute coronary syndromes (ACS), including those undergoing early percutaneous coronary intervention (PCI) and stents implantation is administration of a combination of Aspirin and clopidogrel. Aspirin inhibits platelet thomboxane A2 production and platelet activation, and reduces the risk of recurrent ischemic events in patients at high risk of vascular events by 22% (absolute risk reduction (ARR) about 2%) at the expense of an increase in the odds of major bleeding events by about 60% (Absolute risk increase (ARI) about 0.5%. Clopidogrel inhibits ADP induced platelet activation by blocking the platelet receptor P2Y12, which when combined with Aspirin therapy in patients with ACS, reduces the risk of recurrent ischemic events by a further 20% (ARR about 2.1%), in which the major bleeding events are not increased statistically from aspirin monotherapy.

Clopidogrel (Formula I), chemically named as "(+)-(S)-methyl 2-(2-chlorophenyl)-2-(6,7-dihydrothieno[3,2-c]pyridin-5(4H)-yl)acetate", is currently considered to be the gold standard in the inhibition of blood platelet aggregation. Clopidogrel is marketed as its hydrogen sulphate, hydrochloride, and benzene sulphonate salts. It is widely used for controlling the ischemic events and other cardiovascular disorders efficiently for last 12 years or more.

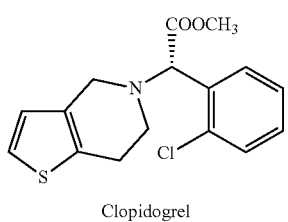

Clopidogrel

However, clopidogrel has several potential limitations. First, the onset of action is delayed and a time lag between administration and therapeutic activity is observed. A therapeutically significant level of 50% inhibition of ADP induced platelet aggregation, as measured by light transmission aggregometry (LTA) (5 µM ADP ex vivo) is not reached until 4-6 hours after administration of a loading dose of 300 mg clopidogrel or until 2 hours by doubling the dose to 600 mg. Secondly, there is a dose ceiling effect, as tripling the dosing from regular dose of 300 mg to 900 mg produces only 60% inhibition of ADP induced platelet aggregation (at 5 µM ADP), and less than 50% inhibition of platelet aggregation (induced by 20 µ·M of ADP (ex vivo)). Third, almost all clinical trials involving clopidogrel reveal that therapeutic levels of platelet inhibition are not achieved in a majority of patients because of large inter-individual variability in response to clopidogrel treatment. This patient population is referred as 'non-responders' or 'poor responders' to clopidogrel. Non-responders make up about 14% of the ethnic Chinese population and 3-4% among Caucasians. Overall, poor responders are close to 23% of the total patient population, and variation of inhibitory activity is reported in about 45% of the total patient population. The ultrarapid metabolism of clopidogrel has been reported in patients having a specific phenotype of CYP isoform (about 4%-18% patients) which leads to more severe bleeding episodes, with higher platelet aggregation. Considering these facts and data from clinical trials, the FDA requires that a boxed warning be included in the label of clopidogrel highlighting the ineffectiveness of clopidogrel in certain classes of patients and suggesting screening of patients for genotyping to identify poor responders to clopidogrel before treatment.

It has been found that the variations in the inhibitory activity of clopidogrel originates from the difference in the activity of liver enzymes that metabolize clopidogrel. Upon ingestion of clopidogrel, it undergoes a series of metabolic reactions to produce metabolites. These reactions are mediated by CYP 450 as well as by action of hepatic human carboxyl esterase (hCE). The metabolic pathway of clopidogrel is set out below. The use of the specific metabolites as therapeutic agents for administration to patients in place of clopidogrel has not been suggested previously.

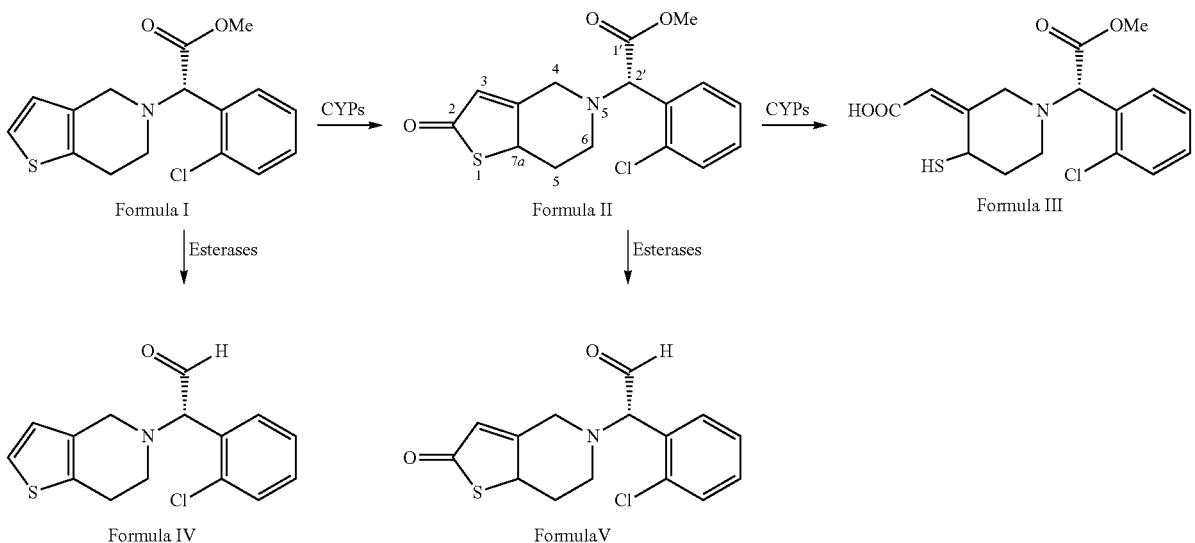

Scheme 1: Metabolic path of clopidogrel

As an alternative to clopidogrel, prasugrel can also be used. However, treatment of patients with prasugrel rendered them susceptible to bleeding episodes, which may be life threatening, restricting its application in patients having a body weight of less than 60 kg body weight and greater than 75 years of age. Prasugrel has also been found to increase liver disease/toxicity in patients who are at risk of cirrhosis and thus pharmacovigilance is suggested by the FDA. As far as these severe side effects are concerned, clopidogrel is comparatively safer, resulting generally in lesser bleeding and liver toxicity. Further, the incidence of cardiovascular deaths is greatly reduced following treatment with clopidogrel in comparison to prasugrel and thus improvements in the efficacy of clopidogrel are likely to reduce the risk of thrombosis and/or embolism in patient groups much better than other structurally modified drugs.

Due to the serious side effects, including the risk of bleeding, associated with the use of prasugrel, it is recommended that prasugrel only be used to achieve an initial thrust of greater inhibition of platelet aggregation. Clopidogrel is then used for subsequent platelet inhibition, after the initial use of prasugrel.

Therefore, there is a need to ameliorate the side effects of clopidogrel or prasugrel. Compounds exhibiting higher onset of action, lower inter-individual variability, better metabolizers status, improved dose ceiling effect, and improved efficacy by increasing inhibitory capacity on ADP induced platelet aggregation are desired.

SUMMARY OF THE INVENTION

The present inventors have discovered that the use of clopidogrel presents substantial clinically significant limitations in inhibiting platelet aggregation safely and rapidly in a consistent manner, though it is considered to be the gold standard among anti-platelet medicine available today. The invention, therefore, aims to provide improved methods for treatment/prophylaxis of thrombosis and embolism, as well as compositions for use in such methods, which ameliorate at least one of the clinical drawbacks of clopidogrel discussed above.

In accordance with a first aspect, the invention provides a method of treatment and/or prophylaxis of thrombosis and/or embolisms in a patient in need of such treatment, while avoiding and/or alleviating the side effects associated with the clopidogrel acid metabolite of Formula IV comprising administering an amount of (S)-oxo-clopidogrel (Formula II) or its derivatives or a pharmaceutically acceptable salt thereof. In an embodiment isolated (S)-oxo-clopidogrel or its derivatives or a pharmaceutically acceptable salt thereof is administered.

In preferred embodiments of this aspect of the present invention, the method achieves a therapeutic effect greater or equivalent to that observed following the administration of a substantially higher dose of clopidogrel.

According to a second aspect of the present invention, there is provided a method of treatment and/or prophylaxis of thrombosis and/or embolisms in a patient in need of such treatment while avoiding and/or alleviating the side effects associated with the clopidogrel acid metabolite of Formula IV comprising administering an amount of the (S)-oxo-metabolite of clopidogrel or its derivatives or a pharmaceutically acceptable salt.

In preferred embodiments of this aspect of the present invention, the method results in the in vivo formation of the active metabolite of clopidogrel at a concentration greater than or equivalent that observed following administration of a substantially higher dose of clopidogrel.

According to a third aspect of the present invention, there is provided an improved method for delivering the active clopidogrel metabolite in vivo for the treatment and/or prophylaxis of thrombosis and/or embolisms in a human in need of such treatment while avoiding or alleviating the side effects associated with inactive clopidogrel acid metabolite of Formula IV, wherein the improvement consists essentially of administering an amount of (S)-oxo-metabolite of clopidogrel or its derivatives or a pharmaceutically acceptable salt.

In all aspects of the present invention, the onset of therapeutic action is at least 50% more rapid than that observed following administration of a substantially higher dose of clopidogrel.

Further, in all aspects of the present invention, various amounts of the oxo-metabolite of clopidogrel or its derivative of Formula IIA may be administered. For example, the amount administered may be 20 to 60 mg and the substantially higher dose of clopidogrel may be 300 mg. Alternatively, the amount of oxo-metabolite or its derivative of Formula IIA may be 35 to 80 mg and the substantially higher dose of clopidogrel may be 600 mg. In alternative embodiments, the amount of oxo-metabolite or its derivative of Formula IIA may be 50 to 100 mg and the substantially higher dose of clopidogrel may be 900 mg. In still further embodiments, the amount of oxo-metabolite or its derivative of Formula IIA may be 5 to 15 mg and the substantially higher dose of clopidogrel may be 75 mg. Alternatively, the amount of oxo-metabolite or its derivative of Formula IIA may be 6 to 20 mg and the substantially higher dose of clopidogrel may be 150 mg.

As an alternative to therapy involving the administration of a series of repeated doses to a patient, a higher loading dose may be followed by one or more maintenance doses. For example, a loading dose of 30-60 mg oxo-clopidogrel or its derivative of Formula IIA may be administered to a patient resulting in greater than 50% inhibition of ADP induced human blood platelet aggregation. In certain embodiments of the present invention, this, or an alternative loading dose may be followed with a maintenance dose of 6-25 mg oxo-clopidogrel or its derivative of Formula IIA is administered to a patient, resulting in greater than 50% inhibition of ADP induced human blood platelet aggregation. The doses discussed herein are for a patient of 60 kg average body weight. It should be understood that dose may be adjusted with respect to body weight of the patient, health/condition condition of the patient, severity of the disease, metabolic profile of the compounds of the present invention. The skilled person in the art has the ability and expertise to adjust the dosage as required.

According to a fourth aspect of the present invention, there is provided a method for minimizing inter individual platelet reactivity variability and metabolic loading in the treatment and/or prophylaxis of thrombosis and/or embolisms observed following administration of a dose of clopidogrel said method comprising administering an effective amount (S)-oxo-clopidogrel metabolite or its derivatives or a pharmaceutically acceptable salt to a patient in need thereof.

The inter-individual variability may be due to CYP450 isoforms and its polymorphic manifestations, for example, in the CYP2C19*2 allele or CYP2C19*17 allele. Additionally or alternatively, the inter-individual variability may be due to P-glycoprotein efflux transports. As such, in an embodiment, the (S)-oxo-clopidogrel is administered to an individual having a CYP450 polymorphism that may cause clopidogrel resistance. Preferably, the CYP450 polymorphism is CYP2C19*2, *1, *2, *3, *4, *5, *6, *7, *8, *9, *10, and/or *17; more preferably CYP2C19*2 and/or *17; and most preferably CYP2C19*2.

According to a fifth aspect of the present invention, there is provided a method for the treatment or prophylaxis of thrombosis or embolisms comprising administration of (S)-oxo-clopidogrel metabolite or its derivatives or a pharmaceutically acceptable salt and a proton pump inhibitor.

In all aspects of the present invention, the methods discussed herein may additionally comprise the step of administration of one or more additional therapeutic agents. These may include, for example, anti-platelet agents selected from aspirin, cilostazol and dipyridamole. These additional agents may be administered simultaneously, sequentially of subsequently to the principal active ingredient.

According to a sixth aspect of the present invention, there are provided compositions for use in the methods described herein. For the avoidance of any doubt, where reference is made to the administration of an amount of active ingredient, this may be comprised within the composition of this aspect of the invention.

According to a seventh aspect of the present invention, there is provided a fixed dose composition of (S)-oxo-clopidogrel or its derivative of Formula IIA characterized in that said composition comprises a dose of 5-35 mg of oxo-clopidogrel or its derivative of Formula IIA.

In a preferred aspect of the present invention, the fixed dose composition comprises a dose of oxo-clopidogrel or its derivative of Formula IIA of 5-15 mg. The fixed dose composition may additionally or alternatively further comprise one or more anti-platelet agents selected from aspirin, cilostazol and dipyridamole.

The advantages of the present invention are realized through use of compounds of Formula II or Formula IIA as well as salts or tautomers thereof

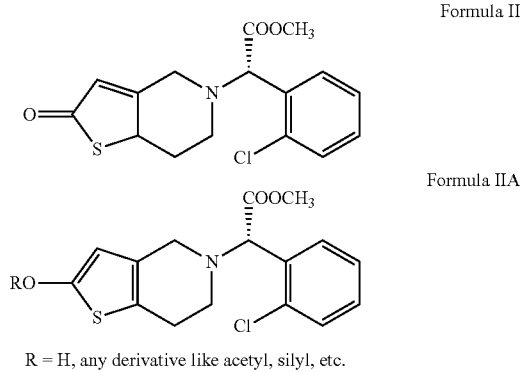

R = H, any derivative like acetyl, silyl, etc.

where R is a hydrogen or a hydrolysable group, such as acyl or alkyl substituted silyl group. The term "acyl" refers to a functional group having the general formula $R^1$—CO—, where $R^1$ can be a aryl, alkyl, alkenyl, or alkynyl. The preferred acyl group is acetyl. The term "alkyl substituted silyl" refers to a functional group having the general formula $R'_3$—Si—, where each of R' is an alkyl. The term "alkyl" refers to a straight or branched hydrocarbon chain radical consisting solely of carbon and hydrogen atoms, containing solely carbon and hydrogen atoms, containing no unsaturation, having, preferably, from one to eight carbon atoms, and which is attached to the rest of the molecule by a single bond, such as illustratively, methyl, ethyl, n-propyl, 1-methylethyl (isopropyl), n-butyl, n-pentyl, and 1,1-dimethylethyl (t-butyl). The term "alkenyl" refers to an aliphatic hydrocarbon group containing a carbon-carbon double bond and which may be a straight or branched or branched chain having, preferably, about 2 to about 10 carbon atoms, e.g., ethenyl, 1-propenyl, 2-propenyl (allyl), iso-propenyl, 2-methyl-1-propenyl, 1-butenyl, 2- and butenyl. The term "alkynyl" refers to a straight or branched chain hydrocarbonyl radicals having at least one carbon-carbon triple bond, and having, preferably, in the range of about 2 up to 12 carbon atoms (with radicals having in the range of about 2 up to 10 carbon atoms being preferred), e.g., ethynyl. The term "aryl" refers to aromatic radicals, preferably, having 6 to 14 carbon atoms such as phenyl, naphthyl, tetrahydronaphthyl, indanyl, biphenyl being optionally further substituted by an $C_1$-$C_6$ alkyl group and/or a halogen atom.

The compound of Formula II is a metabolite of clopidogrel. Despite the structure of this metabolite and its position in the metabolic pathway of clopidogrel being known for almost 20 years, its use as an active agent for the treatment of thrombosis and/or embolisms has not previously been suggested. For Example, a method for preparing such a compound as an intermediate for producing a purportedly efficacious analog of clopidogrel (rather than as an active ingredient in its own right) is disclosed in Example 3 of WO2011/095049. The inventors have identified that the compound of Formula II (as well as its pharmaceutically acceptable salts, tautomers and derivatives of Formula IIA) can advantageously be administered directly to patients in place of clopidogrel and that this ameliorates some if not all of the disadvantages associated with the use of clopidogrel.

This is partly because the metabolite identified as Formula IV in the pathway provided above has been found to be inactive. By administering the compound of Formula II to a patient, the inactive metabolite is not produced in vivo. Further, one less CYP mediated step is required to convert the compound of Formula II (as opposed to clopidogrel) to the active metabolite. Thus, the influence that the patient's ability to metabolize has on efficacy is reduced.

As mentioned above, the use of metabolites of clopidogrel as active agents in their own right, especially Formula II, has not previously been taught or suggested for ameliorating the drawbacks of clopidogrel, and thus, the advantages of doing so, which are discussed herein cannot have been recognized.

The invention provides a method for treatment and/or prophylaxis of thrombosis and/or embolism, where the method comprises administering a predetermined dose of an isolated (S)-isomer of thiolactone compound of Formula II or its tautomer or a derivative thereof in its free form or as a pharmaceutically acceptable salt thereof such that it results in the in vivo formation of the active metabolite of clopidogrel at a concentration equivalent or greater than that achieved through the administration of a substantially greater dose of clopidogrel. In a preferred embodiment, the present invention enables a substantial reduction in the dose of active ingredient required for achieving a therapeutic concentration of active metabolite of clopidogrel compared with administration of conventional, therapeutic doses of clopidogrel. Thus, dose tolerability and efficacy are enhanced significantly.

In another aspect, the present invention can deliver higher concentrations of the active metabolite of clopidogrel in systemic circulation shortly after administration compared to administering clopidogrel. This not only improves the onset of therapeutic action by achieving greater than 50% inhibition of ADP induced platelet aggregation and inter individual variability, but also eliminates the side effects associated with the inactive acid metabolite (Formula IV) and reduces the metabolic load on liver.

In aspects of the present invention, one or more additional active compounds may be administered including antiplatelet agents like aspirin, cilostazol and the like. The antiplatelet agents may operate by a mechanism similar or different to the clopidogrel active metabolite to achieve desired levels of anti-platelet activity. The second or subsequent anti-platelet agent may be administered separately, sequentially or simultaneously with the (S)-isomer of thiolactone compound of Formula II (also referred to herein as (S)-oxo clopidogrel) or its tautomer or a derivative thereof in its free form or as a pharmaceutically acceptable salt thereof.

In aspects of the present invention, a dose ranging from 20-100 mg of compound of Formula II or its tautomers or its derivative of Formula IIA may be administered as an initial loading dose, and if necessary, a maintenance dose as low as 5-35 mg may subsequently be administered such that the systematic concentration of active metabolite is greater than that amount obtained by administering a loading dose of 300-900 mg and a maintenance dose of 75-150 mg of clopidogrel. More preferably the loading dose of the present invention is between 40-75 mg and maintenance dose is between 6-25 mg. Still further lower doses may be administered, if the desired inhibition is equivalent or slightly inferior to that provided by clopidogrel. The doses discussed herein are for a patient of 60 kg average body weight. It should be understood that dose may be adjusted with respect to body weight of the patient, health/condition condition of the patient, severity of the disease, metabolic profile of the compounds of the present invention. The skilled person in the art has the ability and expertise to adjust the dosage as required.

The derivative of Formula IIA may be made from the tautomer of the compound of Formula II, which is preferably an ester (alkyl, aryl, or silyl) derivative. More preferably the derivative is acylated thiolactone of Formula VI.

In aspects of the present invention, there are provided compositions for use in the methods discussed herein. For example, the present invention provides a fixed dose pharmaceutical composition comprising 5 mg to 35 mg of the compound of Formula II or its tautomers or its derivative of Formula IIA or a pharmaceutically acceptable salt thereof and optionally one or more pharmaceutically acceptable excipients. The fixed dose combination of the present invention may be administered along with one or more active compound including antiplatelet agents like aspirin, cilostazol, PPIs (proton pump inhibitors, such as omeprazole), etc., which may operate by a mechanism similar or other than clopidogrel active metabolite.

DETAILED DESCRIPTION OF THE PREFERRED EMBODIMENTS

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

It has now surprisingly been found that it is possible to obtain a higher inhibition of ADP induced platelet aggregation with faster onset, which will ameliorate one or more of the drawbacks of clopidogrel. The present invention meets the long felt need in the treatment of thrombosis and embolism and associated disease conditions. The various aspects of the invention are described in detail with specific embodiments/conditions hereafter.

In accordance with one aspect, the invention provides methods for the treatment and/or prophylaxis of thrombosis and/or embolism, as well as compositions for use in such methods, wherein the method comprises administering an isolated (S)-isomer of thiolactone compound of Formula II (also referred to herein as (S)-oxo-clopidogrel or (S)-oxo metabolite of clopidogrel or (S)-thiolactone) or a derivative thereof in its free form or a pharmaceutically acceptable salt thereof. This results in the in vivo formation of the active metabolite of clopidogrel at a concentration greater or equivalent to the concentration of active metabolite obtained by administration of clopidogrel wherein the dose of said thiolactone or derivative is substantially lower than a corresponding dose of clopidogrel. Preferably the dose of thiolactone (oxo-clopidogrel) or its derivative is lower by two times, more preferably lowered by about 3 times, still preferably lowered by about 5 times and still preferably lowered by about 10 times or more. For example, a dose of the primary active principle of the present invention of 20 to 40 mg, 35 to 80 mg or 50 to 100 mg will provide an improved therapeutic effect or a higher in vivo concentration of the active metabolite of clopidogrel than that observed following a dose of 300 mg, 600 mg or 900 mg of clopidogrel, respectively. Similarly, a dose of the primary active principle of the present invention of 5 to 15 mg or 6 to 30 mg will provide an improved therapeutic effect or a higher in vivo concentration of the active metabolite of clopidogrel than that observed following a dose of 75 mg or 150 mg of clopidogrel, respectively. Accordingly in the present invention, the active metabolite activity obtained is greater or equivalent to clopidogrel at a dose substantially lower than administration of clopidogrel.

It should be understood that thiolactone compound of Formula II exists in tautomeric form of the Formula IIA and the tautomers may be employed in the methods and compositions of the present invention. Derivatives of the thiolactone compound include, but are not limited to, esters or silyl ethers, wherein the hydroxyl group of the compound of Formula IIA is derivatized. The derivatized group is preferably hydrolyzable in vivo by esterases after administration. The preferred ester groups are alkyl (straight chain or branched chain) or aryl esters, more preferably an acetyl or n-butyl/t-butyl esters as expressed in Formula IIA.

The present invention permits the dose of active ingredient required for achieving a therapeutic effect to be reduced compared with administration of clopidogrel. The compounds of Formula II or IIA can be administered as their acid/base addition salts and since the weight of accompanying acid/base changes from one to another, the dose may be calculated based on free thiolactone or its derivative. The doses discussed herein are for a patient of 60 kg average body weight. It should be understood that dose may be adjusted with respect to body weight of the patient, health/condition condition of the patient, severity of the disease, metabolic profile of the compounds of the present invention. The skilled person in the art has the ability and expertise to adjust the dosage as required.

The inventive selection of the compounds of Formula II or IIA significantly contributes to improvements in the antiplatelet treatment compared to the use of clopidogrel and improves its therapeutic efficiency by about 5-15 times as well as reducing the associated toxicity/side effects or metabolic load associated with clopidogrel treatment.

The present invention can provide a therapeutically effective concentration of active metabolite of clopidogrel in a short time after administration, which not only improves the onset of action but also achieves greater than 50% inhibition of ADP induced platelet aggregation. The onset of action can be (as measured by 50% inhibition of ADP induced platelet aggregation) achieved in less than 1 hour, more preferably in 30 minutes, compared to 4-6 hours for clopidogrel. Irrespective of the dose of compounds of Formula II or IIA, the maximum platelet aggregation can be achieved in less than 1 hour after oral administration. This invention thus ameliorates the dose ceiling effect observed with higher doses of clopidogrel and provides significantly higher metabolic output and reduced metabolic loading in liver. Furthermore, as clopidogrel is a P-Glycoprotein (Pgp) substrate, its absorption is influenced by Pgp inhibitors or inducers, which are likely to alter the clinical effects of clopidogrel. This effect should also be reduced to a large extent by the administration of the compositions of the present invention. Additionally, the invention may permit the use of proton pump inhibitors in combination with clopidogrel. It is believed that this is because the role of CYP2C19 (which plays a significant part in the metabolism of clopidogrel) is reduced substantially with the use of the compositions and methods of the present invention, PPIs being inhibitors of CYP2C19.

According to aspects of the present invention, an initial loading dose of between 20-100 mg of compound of Formula II or its derivative (Formula IIA) or a salt thereof may be administered to a human subject in need of treatment or prophylaxis of vascular embolism or thrombosis and, if necessary, a maintenance dose as low as 5-40 mg may be administered such that the concentration of active metabolite of clopidogrel in human plasma is greater than that observed when a loading dose of 300-900 mg and maintenance dose of 75-150 mg of clopidogrel are administered. Preferably a dose of 40-60 mg of the thiolactone compound of Formula II/IIA will achieve greater than 50% inhibition of ADP induced platelet aggregation within an hour, and a maintenance dose of about 6-25 mg is sufficient to maintain platelet inhibition at or above the desired level during the maintenance period. It should, however, be noted that dose adjustments may be made based on the body weight of the patients, which should not be considered to limit the invention.

Apart from increasing the active metabolite concentration and achieving greater platelet inhibitory activity, the compositions and methods of the present invention are thought to reduce the toxicity and/or associated side effects observed due to the formation of clopidogrel acid (Formula IV) following clopidogrel administration. The lethal dose of clopidogrel is about 5000 mg per kg in rat and 90% of clopidogrel is converted to clopidogrel acid in vivo. Thus, it appears that around 90% of the toxicity of clopidogrel may be related to the clopidogrel acid metabolite (Formula IV). Given that the compositions and methods of the present invention advantageously enable the amount of active ingredient administered to patients to be reduced, while also eliminating the formation of clopidogrel acid metabolite following administration, the associated toxicity or adverse side effects will be reduced by at least 9-10 times compared to current clopidogrel therapeutic use.

The compounds employed in the compositions and methods according to present invention are preferably present in the form of their pharmaceutically acceptable salts, preferably acid salts. Examples of such acid addition salts include salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; and salts with organic carboxylic acids, such as acetic acid, propionic acid, butyric acid, fumaric acid, tartaric acid, oxalic acid, malonic acid, maleic acid, malic acid, succinic acid, benzoic acid, mandelic acid, ascorbic acid, lactic acid, gluconic acid or citric acid. Salts, which are not pharmaceutically acceptable may also be employed in the manufacture of the compounds employed in the methods and compositions according to the invention. Preferred salts include hydrochloride, hydrogen sulphate and maleate salts.

The methods and compositions of the present invention may further employ one or more active compounds including antiplatelet agents such as aspirin, cilostazol, dipyridamole and the like which may operate by a mechanism similar or different to the clopidogrel active metabolite to achieve desired levels of anti-platelet activity. The second or subsequent anti-platelet agent may be administered separately, simultaneously or subsequently with the compound of Formula II or its tautomer or a derivative thereof in its free form or as a pharmaceutically acceptable salt thereof. The present invention encompasses such modifications thereof for achieving desired goal of inhibition of platelet aggregation.

In other aspects, the present invention provides a fixed dose pharmaceutical composition of compound of Formula II or its tautomers or its derivative of Formula IIA or a pharmaceutically acceptable salts thereof wherein the dose of said thiolactone is selected from the range of 5 mg to 35 mg and the composition optionally comprises pharmaceutically acceptable excipients. The fixed dose composition of the present invention may comprise or be administered along with one or more active compounds including antiplatelet agents such as aspirin, cilostazol or the like which may operate by a mechanism similar or different to the clopidogrel active metabolite.

The fixed dose pharmaceutical compositions of the invention are preferably administered orally on a daily basis as an immediate release or modified release dosage form.

The dosage form may be formulated as a single unit dosage, as two separate unit dosages, and/or in any of the many variations known in the art, which include, but are not limited to, tablets, pills, hard capsules, soft capsules, pharmaceutical sachets and powders for reconstitution.

The formulations of the invention may further contain water insoluble permeable polymers, herein defined as "modified release polymers", to adjust their release profile. These polymers may either be coated onto formulations such as tablets, microgranules, capsules or pills, or be mixed together with the other ingredients of any of the formulations listed above.

In one embodiment, the pharmaceutical compositions of the present invention are provided in the form of tablets prepared by mixing the active agents with excipients. Typical excipients include diluents, fillers, binders, lubricants, disintegrants, glidants, colorants, pigments, taste masking agents, modified release polymers, sweeteners, plasticizers, and any acceptable auxiliary substances such as absorption enhancers, penetration enhancers, surfactants, co-surfactants, and specialized oils. Examples of excipients include calcium phosphates, such as dibasic calcium phosphate, anhydrous dibasic calcium phosphate, tribasic calcium phosphate, etc.; microcrystalline cellulose, powdered cellulose; starch, pregelatinized starch; sodium starch glycolate; dextrates; mannitol, sorbitol; povidone; ethyl cellulose; lactose; kaolin; silicic acid; lubricants such as magnesium stearate, calcium stearate, stearic acid, mineral oil, glycerin, sodium lauryl sulfate, polyethylene glycol; and/or talc. Sodium starch glycolate, talc and the lubricant magnesium stearate may be used to prepare compositions of the present invention to aid in tablet manufacture. A premix of compound of Formula II/IIA may be obtained by mixing said compound with ingredients and thereafter either directly compressing the mixture into tablets or filling said mixture into capsules optionally along with other suitable ingredients to obtain final dosage form. A unit dose of the free form of a compound of Formula II/IIA may be obtained as a granular premix by suitably processing that compound with acceptable ingredients such as polymers, which can be directly compressed or formulated with additional excipients.

The compositions and methods of the present invention may be employed in the prevention and/or treatment of pathological states such as disorders of the cardiovascular and cerebrovascular system such as the thromboembolic disorders associated with atherosclerosis or with diabetes such as unstable angina, cerebral attack, restenosis following angioplasty, endarterectomy or fitting of metallic endovascular prostheses, with rethrombosis following thrombolysis, with infarction, with dementia of ischaemic origin, with peripheral arterial diseases, with haemodialyses, with auricular fibrillations or during the use of vascular prostheses or aortocoronary bypasses or in relation to stable or unstable anger.

The compounds of Formula II or its acid salts can be obtained by any method disclosed in U.S. Pat. Nos. 4,740,510 and 5,190,938, which are incorporated herein by reference, for its various ester derivatives. Chiral isomer separation may be performed by any known racemic separation method using chiral acids or the isomer may be stereo-selectively synthesized.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in those examples.

Example 1

(±)-Thiolactone Compound of Formula II 10.43 g potassium bicarbonate, 7.852 g sodium iodide and 11 gm methyl-2-bromo-2-(chlorphenyl acetate were added to a solution of 10 gm of 5,6,7,7a-tetrahydro-4H-thieno[3,2-c] pyridine-2-one hydrochloride in 100 ml dimethylformamide. The medium is heated to 60° C. for 2 hours and then poured into 600 ml water. The product is extracted using ethyl acetate.

Example 2

Methyl-(R)-2-hydroxy-2-(2-chlorophenyl)acetate

In a 1 L flask, 120 g (0.643 mole) of (R)-2-chloromandelic acid, 480 ml methanol and 4.8 g concentrated sulfuric acid were added. The solution is then heated to reflux for 2 hours and excess methanol is distilled under vacuum. The oily residue was taken in 650 ml chloroform and washed with 240 gm aqueous solution of 10% potassium carbonate and concentrated under vacuum. 124.4 gm of methyl-(R)-2-hydroxy-2-(2-chlorophenyl)acetate was obtained in the form of a colorless oil.

Example 3

Methyl(R)-2-(4-nitrophenylsulfonyloxy)-2(2-chlorophenyl)acetate

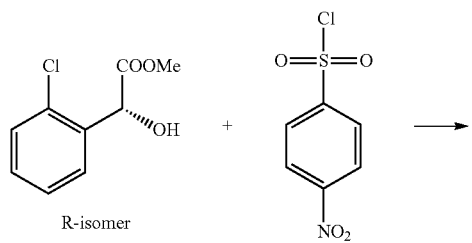

R-isomer

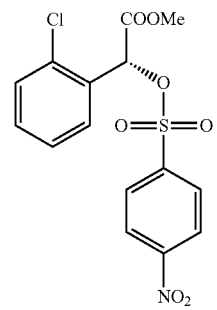

0.72 g (6 mmoles; 0.1 equivalent) of 4-dimethylaminopyridine, 12.0 g (60 mmoles; 1 equivalent) of methyl(R)-2-hydroxy-2(2-chlorophenyl)acetate and 7.8 g (78 mmoles; 1.3 equivalent) of triethylamine and 20 ml of dichloromethane were added to a dry reaction flask. The colorless solution obtained was cooled to 0° C. and then, operating at this temperature, 13.14 g (60 mmoles; 1 equivalent) of 4-nitrobenzenesulfonyl chloride as a solution in 30 ml of dichloromethane was added. The reaction mixture was stirred for 3 hours at 0° C. and 240 ml of 1N hydrochloric acid and 240 ml of dichloromethane was added drop wise, while stirring this mixture. After decanting, the dichloromethane phase is washed with dilute hydrochloric acid and then with water, before being concentrated under reduced pressure. An analytically pure sample is obtained after purifying on a silica column. In this manner, methyl(R)-2-(4-nitrophenylsulfonyloxy)-2(2-chlorophenyl)acetate is obtained: Yield: 98%. Optical purity: 99%.

Example 4

Methyl(S)-2(2-chlorophenyl)-2-(2,4,5,6,7,7a-hexahydrothieno[3,2-c]-5-pyridin-2-one)acetate

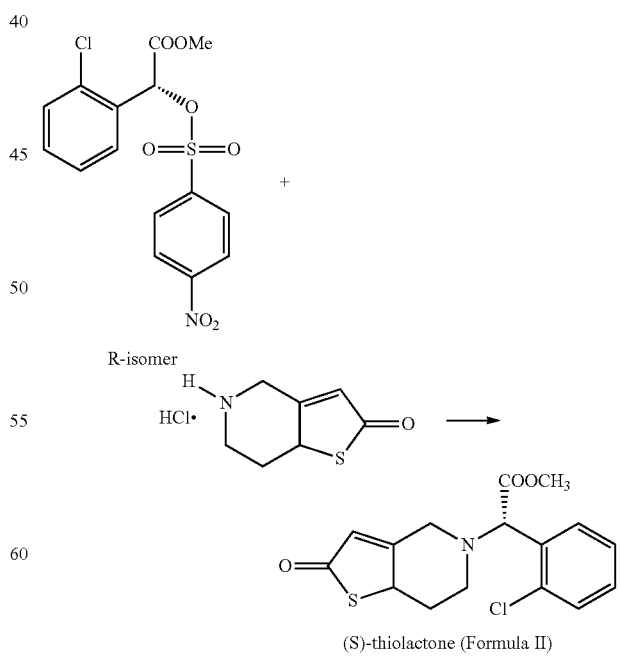

In a dry, 50-ml reaction flask, 5 mmoles of 5,6,7,7a-tetrahydro-4H-thieno[3,2-c]pyridine-2-one as a solution 7.5 ml of dichloromethane (prepared from hydrochloride salt after neutralization with aq. potassium carbonate) and 2.85 g of a 30% aqueous solution of potassium carbonate were mixed. After stirring for 10 minutes, 5 mmoles of the Methyl(R)-2-(4-nitrophenylsulfonyloxy)-2-(2-chlorophenyl)acetate as a solution in 2.5 ml of dichloromethane was added. The two-phase medium thus obtained was heated under reflux for 1 hour and then cooled to 7° C. and decanted. After work-up, (S)-isomer of title Methyl(S)-2(2-chlorophenyl)-2-(2,4,5,6, 7,7a-hexhydrothieno[3,2-c]-5-pyridin-2-one)acetate [(S)-thiolactone of Formula II] was obtained. Optical purity (2'S) >98%.

Example 5

Methyl(S)-2(2-chlorophenyl)-2-(2,4,5,6,7,7a-hexahydrothieno[3,2-c]-5-pyridin-2-one)acetate

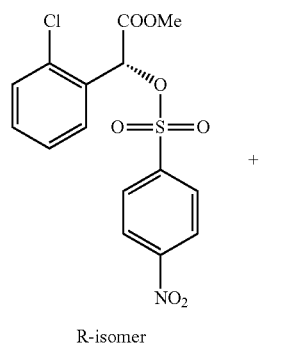

R-isomer

+

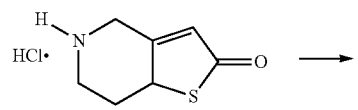

In a dry, 250-ml reaction flask, 5.94 gm (31.1 mmoles) of 5,6,7,7a-tetrahydro-4H-thieno[3,2-c]pyridin-2-one hydrochloride, 39 ml of dichloromethane and 29.8 g of a 30% aqueous solution of potassium carbonate were mixed. After stirring for 10 minutes, 10 gm of (25.9 mmoles of Methyl(R)-2-(4-nitrophenylsulfonyloxy)-2-(2-chlorophenyl)acetate as a solution in 13 ml of dichloromethane was added. The two-phase medium thus obtained was heated under reflux for 6 hrs. Then cooled to about 30° C. Filtered the R.M. Filtrate was having two layers. MDC layer was washed with brine solution. Dried over anhydrous sodium sulfate. After concentration Methyl(S)-2(2-chlorophenyl)-2-(2,4,5,6,7,7a-hexhydrothieno[3,2-c]-5-pyrid-in-2-one)acetate [(S)-thiolactone of Formula II] was obtained.

Example 6

Acetyl Ester of Compound of Formula II

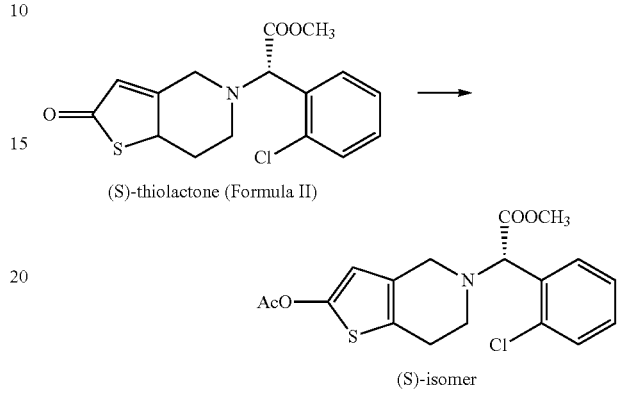

83.85 g of (S)-thiolactone compound of formula II obtained above was dissolved in 120 ml of isopropenyl acetate and mixed with 7.8 g of p-toluene sulfonic acid. The mixture is heated to 90° C. under stirring for 6 hours. The reaction mass then cooled to about 20.degree. C. and 20 ml of water was added to the mixture. The mixture is then basified by addition of saturated aqueous sodium bicarbonate solution and extracted with ethyl acetate. Ethyl acetate layer is further washed twice with water and distilled under vacuum to remove ethyl acetate. The residue obtained was dissolved in acetone and HCl gas was passed into the solution under cooling. The obtained precipitate was filtered, recrystallized from acetone to get hydrochloride salt of acetyl derivative. Optical purity >99.5%

Example 7

Acetyl Ester of Compound of Formula II

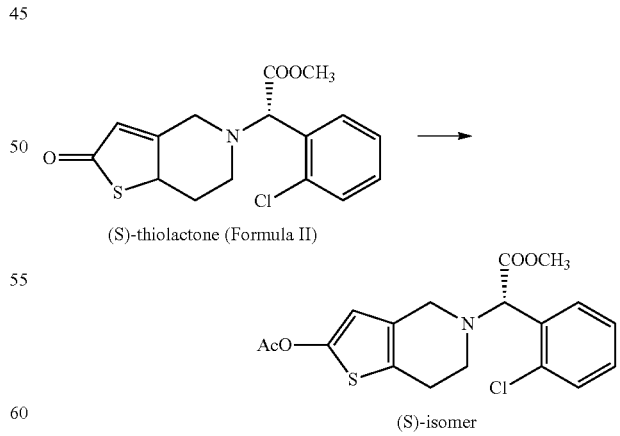

25 g (74 mmole) of (S)-thiolactone compound of formula II was taken in 250 ml of acetonitrile. The mixture was cooled. Then added 9.03 gm (95.1 mmole) of triethylamine under stirring followed by addition of 9.11 gm (95.1 mmole) of acetic anhydride under cooling. After addition reaction mass was stirred at ambient temperature. Then distilled off acetonitrile. Residue was dissolved in ethylacetate, washed with water and concentrated. The residue obtained was dissolved in isopropanol. Added 1 mole equivalent of isopropanol.HCl solution. The obtained precipitate was filtered to get hydrochloride salt of acetyl derivative.

Example 8

Pharmacology and Toxicology

The pharmacological and toxicological results which are reported below demonstrate the properties of the compositions of the invention both from the point of view of toxicity and tolerance, and from the point of view of their activities, particularly inhibition of platelet and thrombotic aggregation.

A. Toxicological Study

The compositions of the invention demonstrate excellent tolerance and low toxicity. In addition, the tests carried out on the acute, chronic, subchronic and delayed toxicities in different species of animals, have not demonstrated any local or general reaction, disturbance or anomaly in the biochemical, macroscopic or microscopic examinations carried out during these experiments.

B. Pharmacological Study

The platelet aggregation inhibiting activity and the toxicity of the inventive compositions were compared to those of the clopidogrel as described in the French Pat. No. 82,12599 (Publication No. 2 530 247), which is incorporated herein by reference.

The platelet aggregation inhibiting activities and the antithrombotic activities of the compounds were studied in the rat by standard methods.

1. Measurement of Platelet Aggregation with ADP

The activity on the aggregation of plates induced by ADP or collagen was determined ex-vivo.

The products dissolved in ethanol (200 mg/ml) and diluted in water containing gum arabic (5%-wt/v) were administered by the oral route to groups of five female rats of the CD-COBS strain, weighing 250-300 g, in amounts of 10 ml of suspension per kilogram two hours before blood samples were taken.

The blood samples were taken from animals anesthetized with diethyl ether by puncture of the abdominal aorta and placed over a 3.8% aqueous solution of sodium citrate (1 vol/9 volumes of blood). The platelet-rich plasma was then isolated by centrifugation at 200 g for 10 minutes.

Aggregation is induced by the addition of 2 µl of aggregating solution to 400 µl of platelet-rich plasma. The aggregating solutions used were: a 500 µM aqueous solution of ADP (final concentration 2.5 µM).

The aggregation of the platelets was monitored as described by Born (Nature 194, p. 927 (1967)), which is incorporated herein by reference, using a Coultronics® aggregometer at a temperature of 37° C. and agitation of 900 rpm.

For aggregation with ADP, the aggregometer generates a curve representing a platelet aggregation as measured by a change in optical density. The height of this curve is defined as the height of aggregation. The percentage of aggregation is the relation between the aggregation height measured and the height corresponding to 100% aggregation×100. The percentage of inhibition is determined by the relation:

$$\frac{\text{Control aggregation height} - \text{produced aggregation height}}{\text{Control aggregation height}} \times 100$$

The results obtained for the aggregation with ADP are shown in Table 1 and they demonstrate that activity of the molecule. The controls are without drug.

TABLE 1

| Product | Dose (mg/kg) | Qty of base administered (mg/kg) | % aggregation* | % inhibition | P** |
|---|---|---|---|---|---|
| Control | | | 103 ± 3 | | |
| Clopidogrel bisulphate | 12.5 | 9.813 | 19 ± 4 | 82 | 0.001 |
| | 25 | 19.225 | 11 ± 1 | 89 | 0.001 |
| Control | | | 94 ± 1 | | |
| Thiolactone | 2.5 | 2.5 | 4 ± 2 | 95 | 0.001 |

*height, Mean of results ± standard deviation
**Students test

2. Anti-Thrombotic Activity

The antithrombotic activity has also been studied in the test of venous thrombosis on a screw thread described by Kumada T. et al. in Thromb. Res 18 p. 189 (1980).

Female rats of the same type as those previously described, in groups of 10 animals, were anesthetized with diethyl ether and their vena cava was isolated after abdominal incision.

A metallic screw thread 21 mm long consisting of a dentist's drill, marketed by Dyna (France) size No. 30, was introduced into the lumen of this vein just below the renal bifurcation descending towards the iliac veins, without damaging the wall; 19 to 20 mm of the length of the screw thread are implanted and the remaining 1 mm protrudes through the closed stomach into the exterior.

The thrombi formed rapidly and five hours later, under pentobarbital anesthesia, the abdomen is reopened and ligatures are placed above and below the screw thread which is withdrawn after longitudinal incision of the vein and the isolated thrombus is weighed.

The results which are presented in Table 2 show that thiolactone of Formula II is superior to clopidogrel. The control is without drug.

TABLE 2

| Product | Dose (mg/kg) | Qty of base administered (mg/kg) | Weight of thrombus* (mg) | % inhibition | P** |
|---|---|---|---|---|---|
| Control | | | 3.9 ± 0.3 | | |
| Ciopidogrel bissulphate | 10 | 7.69 | 1.26 ± 0.19 | 67 | 0.001 |
| | 20 | 15.38 | 1.20 ± 0.13 | 69 | 0.001 |
| Control | | | 4.18 ± 0.31 | | |
| Thiolactone | 12.5 | 12.5 | 1.18 ± 0.18 | 76 | 0.001 |

*Mean of results ± standard deviation;
**Students test

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. A composition comprising (S)-oxo-clopidogrel or a compound of Formula IIA

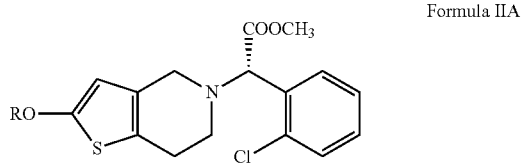

Formula IIA or pharmaceutically acceptable salts thereof, wherein R is hydrogen or an alkyl substituted silyl group.

2. The composition of claim 1, further comprising a proton pump inhibitor.

3. The composition of claim 1, further comprising a proton pump inhibitor compound, or an anti-platelet agent selected from the group consisting of aspirin, cilostazol and dipyridamol.

4. The composition of claim 1, wherein R is an alkyl substituted silyl group having the formula $R'_3$-Si— wherein R' is a straight or branched alkyl having from one to eight carbon atoms.

5. The composition of claim 4, wherein R' is selected from the group consisting of methyl, ethyl, n-propyl, 1-methylethyl, n-butyl, n-pentyl and 1,1-dimethylethyl.

6. The composition of claim 1, wherein said composition ameliorates clopidogrel resistance.

7. A fixed dose composition of (S)-oxo-clopidogrel or a compound of Formula IIA

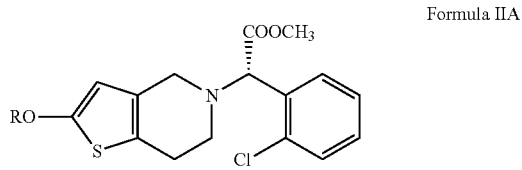

Formula IIA or pharmaceutically acceptable salts thereof; wherein R is hydrogen or an alkyl substituted silyl group; characterized in that said composition comprises a dose of 5 mg-35 mg of said (S)-oxo-clopidogrel or said Formula IIA or pharmaceutically acceptable salts thereof, and a pharmaceutically acceptable excipient.

8. The fixed dose composition of claim 7, further comprising a proton pump inhibitor compound, or an anti-platelet agent selected from the group consisting of aspirin, cilostazol and dipyridamol.

9. The fixed dose composition of claim 7, wherein the composition reduces or alleviates inter individual platelet response variability and metabolic loading in humans in the treatment or prophylaxis of thrombosis or embolisms observed following administration of clopidogrel.

10. A pharmaceutical composition for the treatment or prophylaxis of thrombosis or embolisms in a clopidogrel non-responder- or poor-responder-patient in need of such treatment, said composition comprising (S)-oxo-clopidogrel or a compound of Formula IIA

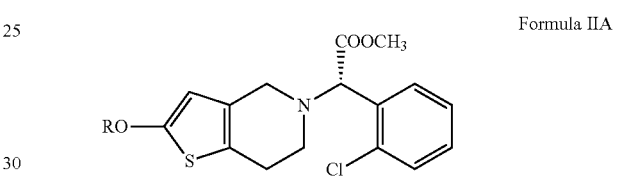

Formula IIA or pharmaceutically acceptable salts thereof, wherein R is hydrogen or an alkyl substituted silyl group.

11. The pharmaceutical composition of claim 10, further comprising a proton pump inhibitor compound, or an anti-platelet agent selected from the group consisting of aspirin, cilostazol and dipyridamol.

* * * * *